United States Patent
Kasahara et al.

(10) Patent No.: US 6,863,674 B2
(45) Date of Patent: Mar. 8, 2005

(54) OPERATING TROCAR

(75) Inventors: Hideyuki Kasahara, Musashino (JP); Takahiro Kogasaka, Hino (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/328,237

(22) Filed: Dec. 23, 2002

(65) Prior Publication Data
US 2003/0125666 A1 Jul. 3, 2003

(30) Foreign Application Priority Data
Dec. 28, 2001 (JP) .................................. 2001-401943

(51) Int. Cl.⁷ ............................................ A61F 11/00
(52) U.S. Cl. .................. 606/108; 600/114; 604/174; 604/179; 604/180; 604/117
(58) Field of Search .................. 606/108, 170, 606/167, 184–186, 1; 604/117, 164.01, 264, 174–180, 104–109, 164.04, 169.09, 167.01, 167.02, 167.06; 128/DIG. 26; 600/114

(56) References Cited

U.S. PATENT DOCUMENTS

| | | | |
|---|---|---|---|
| 4,380,234 A | * | 4/1983 | Kamen ........................ 604/120 |
| 4,781,694 A | | 11/1988 | Branemark et al. |
| 5,213,567 A | | 5/1993 | Masaki |
| 5,267,970 A | | 12/1993 | Chin et al. |
| 5,279,575 A | | 1/1994 | Sugarbaker |
| 5,375,588 A | * | 12/1994 | Yoon ........................... 600/114 |
| 5,391,156 A | | 2/1995 | Hildwein et al. |
| 5,456,673 A | | 10/1995 | Ziegler et al. |
| 5,554,106 A | * | 9/1996 | Layman-Spillar et al. .... 602/42 |
| 5,569,207 A | * | 10/1996 | Gisselberg et al. ......... 604/175 |
| 5,626,597 A | | 5/1997 | Urban et al. |
| 5,728,103 A | * | 3/1998 | Picha et al. ................ 606/108 |
| 5,897,531 A | | 4/1999 | Amirana |
| 6,554,823 B2 | * | 4/2003 | Palmer et al. ................. 606/1 |

FOREIGN PATENT DOCUMENTS

| | | |
|---|---|---|
| DE | 195 23 685 A1 | 1/1997 |
| DE | 197 26 141 A1 | 1/1999 |
| EP | 0 577 400 A1 | 1/1994 |
| EP | 0 637 435 A1 | 2/1995 |
| FR | 2 727 849 | 6/1996 |
| JP | 3024069 | 2/1996 |
| JP | 9-28666 | 2/1997 |
| WO | WO 01/08563 A2 | 2/2001 |

* cited by examiner

Primary Examiner—Cris L. Rodriguez
(74) Attorney, Agent, or Firm—Scully, Scott, Murphy & Presser

(57) ABSTRACT

An operating trocar according to the invention includes a guide tube inserted through a body surface to introduce an endoscope and an operating instrument into a living body, and a flange portion provided on the guide tube to make a predetermined angle with a plane approximately perpendicular to an axial direction of the guide tube, the flange portion being fixed to an outer surface of the body surface. Preferably, the operating trocar also includes a gastightness retaining portion provided in the guide tube to retain gastightness between a circumferential surface of an internal hole of the guide tube and a medical instrument such as an endoscope and an operating instrument inserted in the internal hole of the guide tube.

11 Claims, 12 Drawing Sheets

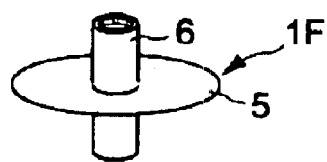  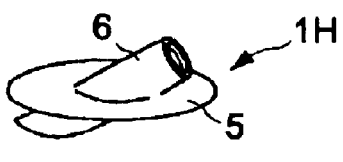
FIG. 15A  FIG. 15B  FIG. 15C
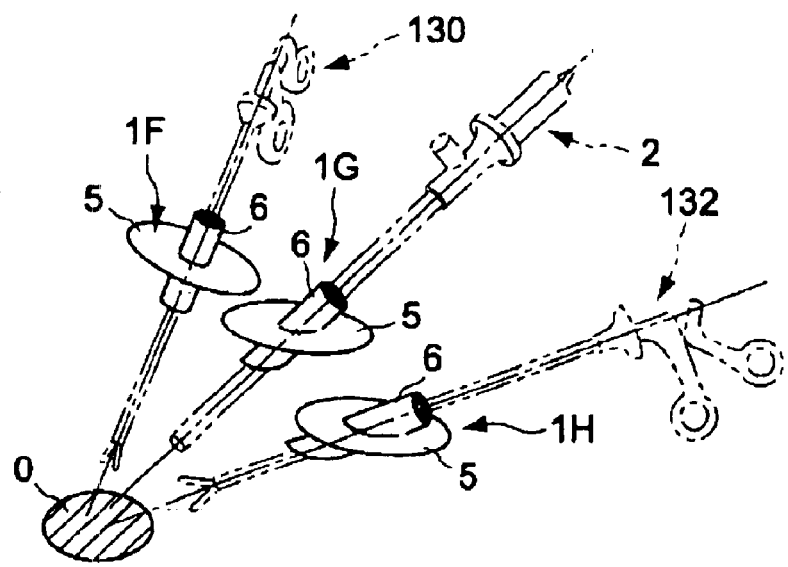
FIG. 16

OPERATING TROCAR

CROSS-REFERENCE TO RELATED APPLICATION

This application is based upon and claims the benefit of priority from the prior Japanese Patent Application No. 2001-401943, filed Dec. 28, 2001, the entire contents of the application are incorporated herein by reference.

BACKGROUND OF THE INVENTION

1. Field of the Invention

The present invention relates to a trocar for introducing an endoscope, A therapeutic instrument and the like into a living body during operation. A trocar according to the invention is suited to, for example, endoscopic surgical operation.

2. Description of the Related Art

Various types of trocars for introducing endoscopes, therapeutic instruments and the like into living bodies are known.

Japanese Utility Model Registration No. 3024069 discloses an art of providing a balloon-like stopper on a trocar to prevent the trocar from coming off.

Japanese Patent Laid-Open No. 28666/1997 discloses an art of preventing a trocar from coming off, by expanding an expanding portion in a body cavity.

BRIEF SUMMARY OF THE INVENTION

A trocar according to the invention includes a guide tube for introducing a medical instrument into a living body and a flange provided on an outer circumference of the guide tube at a location other than opposite ends thereof, the flange having a surface which comes into contact with an outer surface of the living body and which is oblique with respect to an axis of the guide tube.

In addition, it is preferable that at least a part of the trocar be formed of an elastic material so that the trocar can follow the movement of the medical instrument.

In the trocar, it is general to integrate the guide tube and the flange, bat the guide tube and the flange may also be constructed to be removably secured to each other so that the trocar can be conveniently cleaned and stored. In addition, this construction makes it easy to manufacture trocars.

In addition, in order to increase the adhesion between the flange and the outer surface of the living body, it, is preferable to provide a fixing portion (for example, an adhesive layer provided on the surface of the flange which comes into contact with the outer surface of the living body, an adhesive sheet wider in area than the flange and stuck to the surface of the flange opposite to the surface which comes into contact with the outer surface of the living body, or a fixing band extending from the flange). Holes through which to pass sutures may also be provided in the flange in order to fix the trocar to the living body In the guide tube, a gastightness retaining member (for example, an O-ring or a valve) may also be provided so that the gastightness of a body cavity can be efficiently retained.

It is preferable that the wall thickness of the guide tube be made a thickness suited for the insertion of the guide tube and the wall thickness of the flange be made a thickness which enables the flange to easily adhere to the body surface. Accordingly, in general, both wall thicknesses differ from each other, and in many cases, the flange is thinner in wall thickness than the guide tube.

Some of the above-described additional features of the invention can also be applied to known trocars.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

FIGS. 15A to 15C are perspective views showing a plurality of trocars which differ in the inclination angles of their guide tubes to their flanges;

FIG. 16 is a perspective view showing the manner in which the trocars shown in FIGS. 15A to 15C are used.

DETAILED DESCRIPTION OF THE INVENTION

Preferred embodiments of the invention will be described below with reference to the accompanying drawings.

Figure 1:
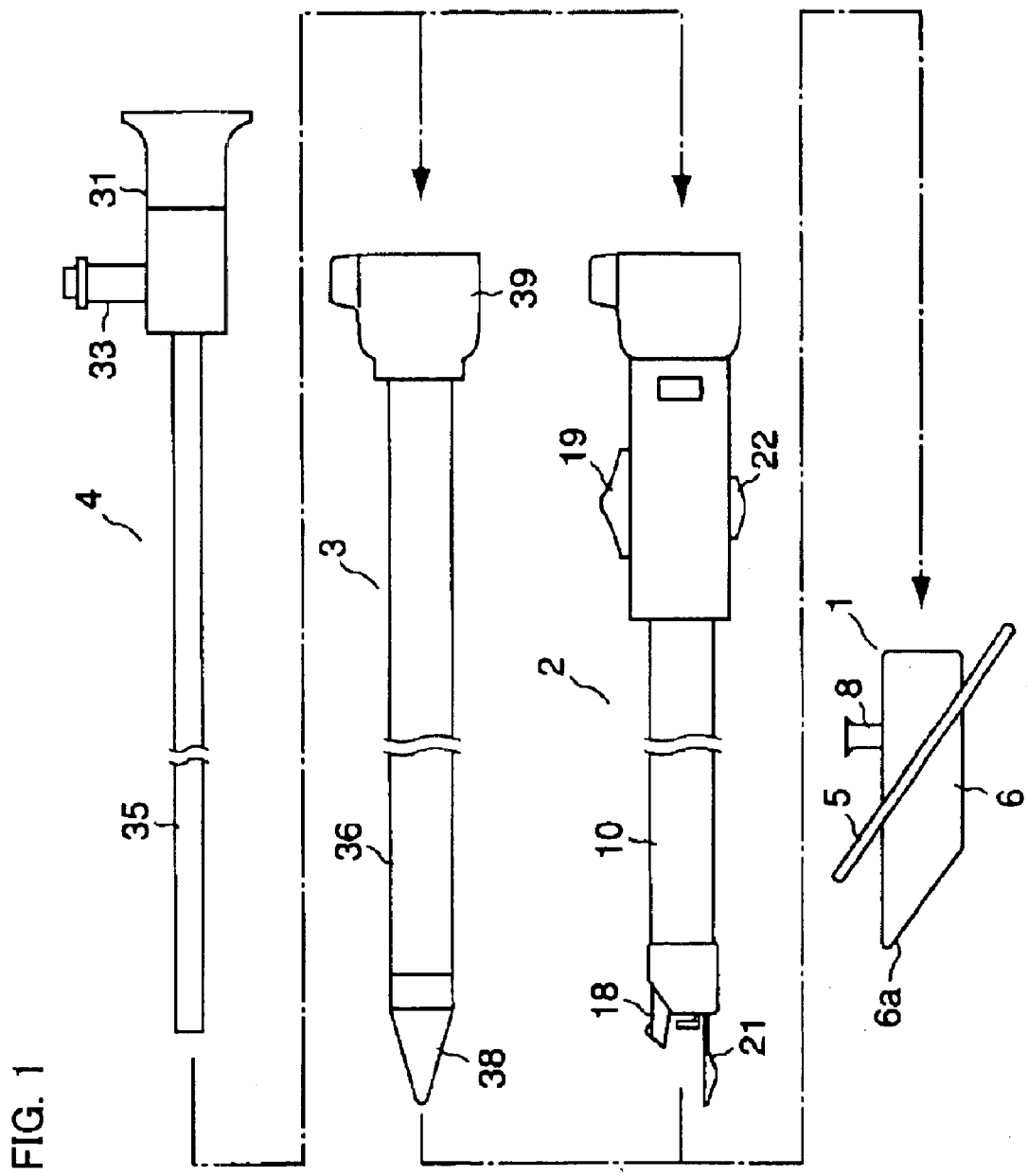
FIG. 1 is an exploded side view of a blood vessel harvester including a trocar according to a first embodiment of the invention.

FIG. 1 shows an endoscopic blood vessel harvester including a trocar for endoscopic operation according to a first embodiment of the invention. As shown, the endoscopic blood vessel harvester is made of a trocar 1, a therapeutic sheath 2, a dissector 3 which serves as expanding means, and a rigid scope 4 which serves as an endoscope.

Figure 2A:
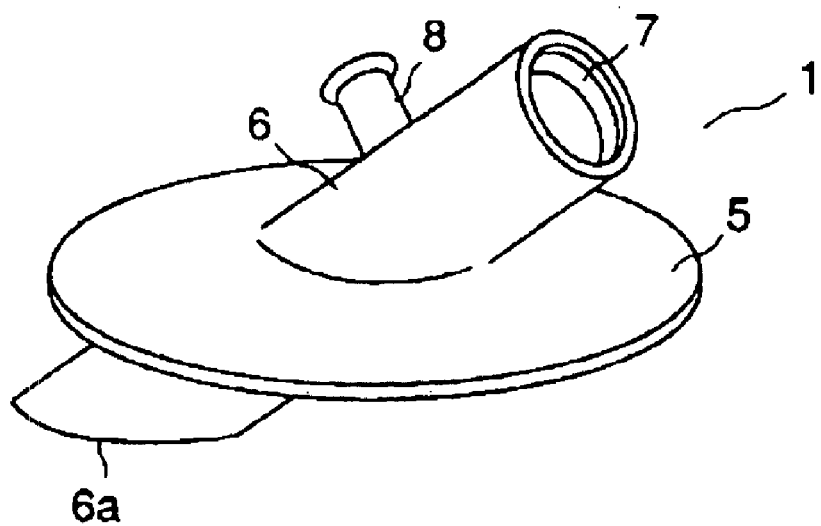
FIG. 2A is a perspective view of the trocar according to the first embodiment.
Figure 2B:
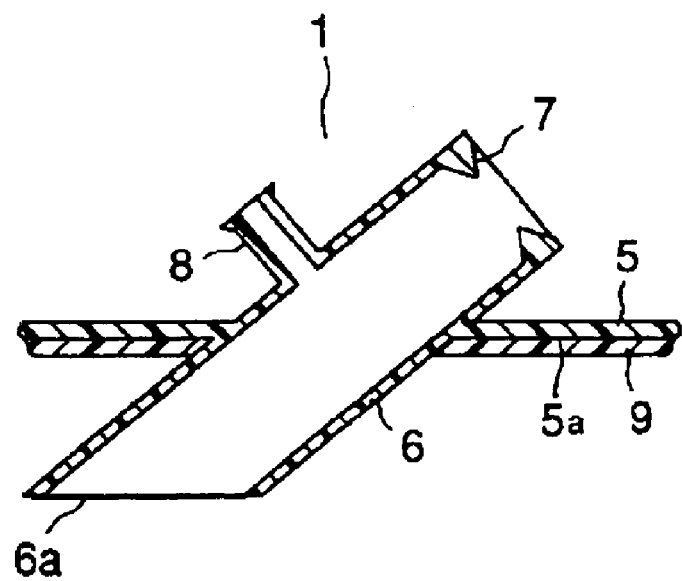
FIG. 2B is a longitudinal sectional view of the same trocar.

As shown in FIGS. 2A and 2B, the trocar 1 comprises a flange 5 which has an approximately disk like shape and is provided with a cylindrical guide tube 6 in such a manner that the guide tube 6 is obliquely inserted through the flange 5. In many cases, trocars are integrally molded from a synthetic resin material (for example, polysulfone), or formed of a metal (for example, SUS 304 stainless steel). In the first embodiment, the trocar 1 is formed of an elastic material (for example, silicone rubber) so that the trocar 1 has elasticity. As a matter of course, when the trocar 1 is to be given elasticity, the whole of the trocar 1 need not be formed of an elastic material, and only the necessary part of the trocar 1 may be formed of an elastic material. In many cases, the portions of guide tubes that are to be inserted into the bodies of patients do not need great elasticity, but flange portions which come into contact with the body surfaces of patients need great elasticity. In view of this situation, an elastic material can also be used mainly for the flange portions.

The outer surface of the guide tube 6 is covered with a lubricating coating for improving the smoothness of insertion of the guide tube 6. A tip 6a of this guide tube 6 is cut at an acute angle, and the end surface of the tip 6a is formed approximately in parallel with the flange 5.

In addition, the inner circumferential surface of the proximal end of the guide tube 6 is integrally provided with a gastight ring portion 7 which serves as a gastightness retaining member (a sealing member), and an intermediate portion of the guide tube 6 is integrally provided with a gas feed connecting portion 8. The gastightness retaining member is provided on a side closer to the proximal end than the gas feed connecting portion 8 (on a side far from the interior of a patient). This construction aims to prevent a gas fed into the trocar 1 through the gas feed connecting portion 8 from leaking out of the trocar 1 at the proximal end. In addition, the bottom or contact surface of the flange 5a (the surface of the flange 5 which comes into contact with the patient) is provided with an adhesive layer 9 (for example, adhesive tape) so that the trocar 1 can be adhesively fixed to the skin of the patient.

As shown in FIG. 1, the therapeutic sheath 2 has a sheath body 10. The sheath body 10 has the form of a straight cylinder made of a synthetic resin material or the like, and the outer surface of the sheath body 10 is covered with a lubricating coating for improving the smoothness of insertion of the sheath body 10. The sheath body 10 is constructed so that a rigid scope 4 can be freely inserted into and extracted from the interior of the sheath body 10. In addition, the sheath body 10 is provided with a first therapeutic instrument channel and a second therapeutic instrument channel. A bipolar cutter 18 is inserted through the first therapeutic instrument channel as a high-frequency therapeutic instrument. The bipolar cutter 18 is constructed to move axially back and forth when a therapeutic instrument manipulating portion 19 is slid axially back and forth. In addition, a blood vessel holder 21 is inserted through the second therapeutic instrument channel, and is constructed to move axially back and forth when a holder manipulating portion 22 is slid axially back and forth.

The dissector 3 has a straight cylindrical inserting tube 36, as shown in FIG. 1. An axial portion of this inserting tube 36 is provided with an inserting passage through which to insert an inserting portion 35 of the rigid scope 4. The outer surface of the inserting tube 36 is covered with a lubricating coating for improving the smoothness of insertion of the inserting tube 36. A dissecting portion 38 made of a transparent synthetic resin material formed into a conical shape is fixed to the distal end of the inserting tube 36.

The rigid scope 4 has the inserting portion 35 and an eyepiece portion 31, and a light guide connecting portion 33 is provided on the side of the rigid scope 4.

A case where the blood vessel harvester constructed in the above-described manner is used to extract an extraction target blood vessel (hereinafter referred to simply as a blood vessel) along the full length thereof will be described below with illustrative reference to a great saphenous vein which extends from the inguinal region of the thigh to the ankle of either of the lower limbs.

Figure 3:
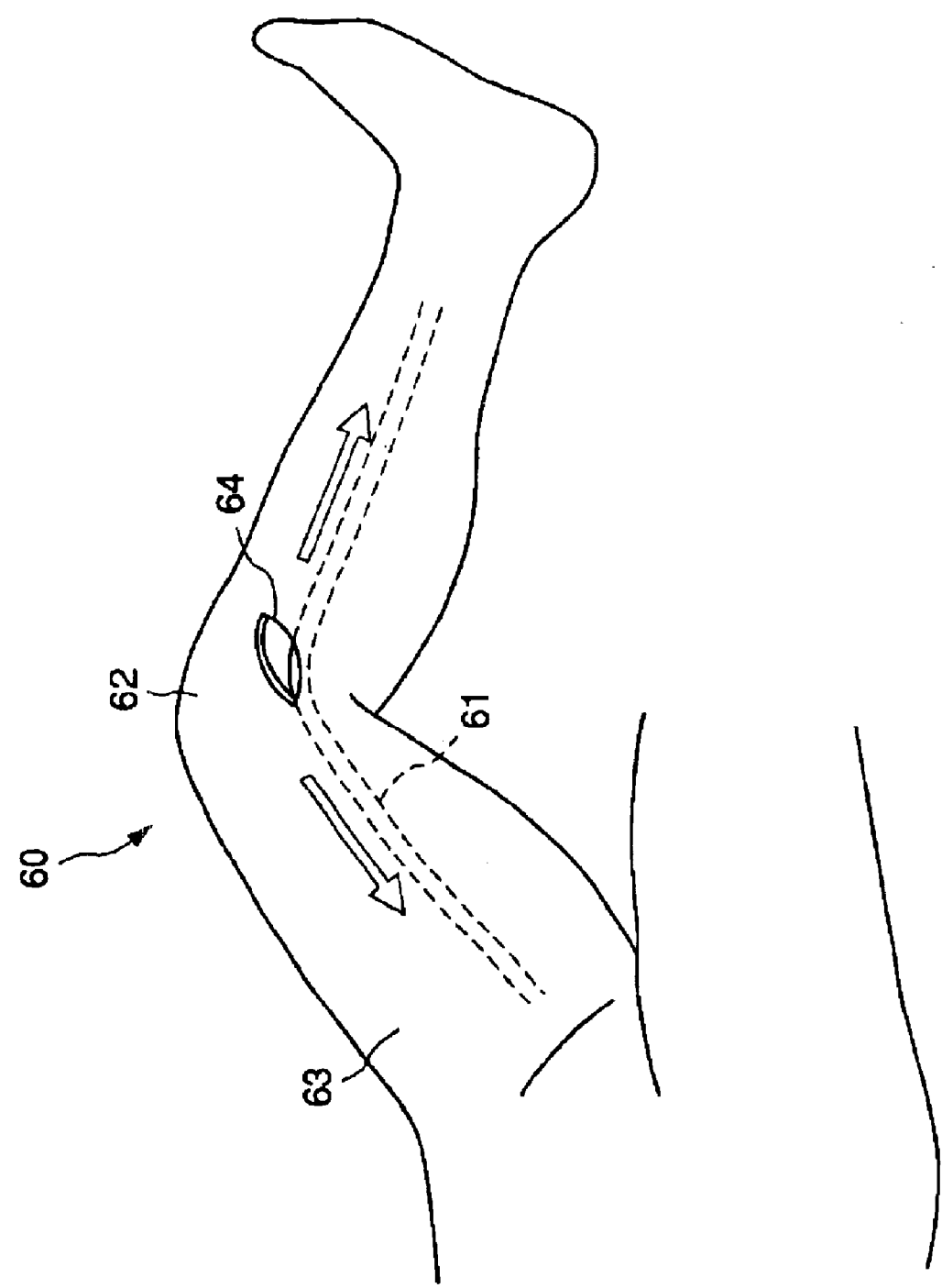
FIG. 3 is a view showing the state in which a dissected portion of skin is formed in a lower limb according to the first embodiment.

FIG. 3 shows a lower limb 60, and reference numeral 61 denotes a blood vessel. A dissected portion of skin 64 is provided between a knee 62 and an inguinal region 63. As shown, when an operator is to extract the blood vessel 61 between the knee 62 and the inguinal region 63, the operator provides the dissected portion of skin 64 at one location of the knee 62 immediately above the blood vessel 61 by means of a scalpel or the like.

Then, the operator exposes the blood vessel 61 in the dissected portion of skin 64 by means of the dissector 3 or the like. Further, the operator dissects tissues immediately above the blood vessel 61 by means of the similar dissector 3 or the like over a distance from the dissected portion of skin 64, which distance is observable with the naked eyes.

Figure 5:
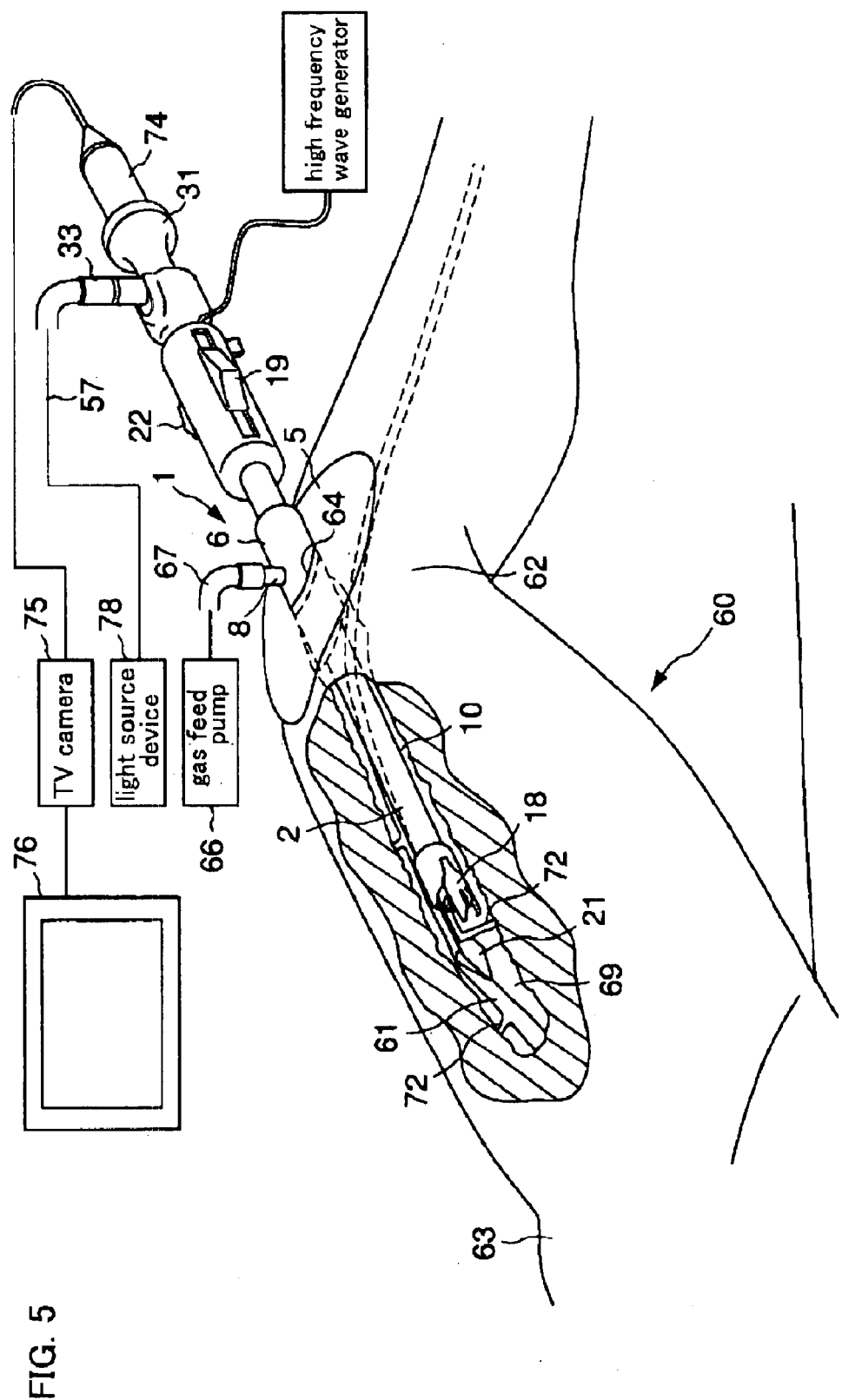
FIG. 5 is a general construction diagram showing the state in which a therapeutic sheath is inserted into the cavity by using the trocar in the first embodiment as a guide.

FIG. 5 shows the manner in which the therapeutic sheath 2 having the rigid scope 4 inserted inside is inserted through the trocar 1. In the combination shown in FIG. 5, the dissector 3 may also be substituted for the therapeutic sheath 2. In this substituted combination, the operator proceeds dissection with the dissector 3. An image of the status of dissection through the dissecting portion 38 of the dissector 3 is picked up by a TV camera 75 via a TV camera head 74 connected to the eyepiece portion 31 of the rigid scope 4, and the picked-up image is displayed on a monitor 76 as a monitor image.

Figure 4:
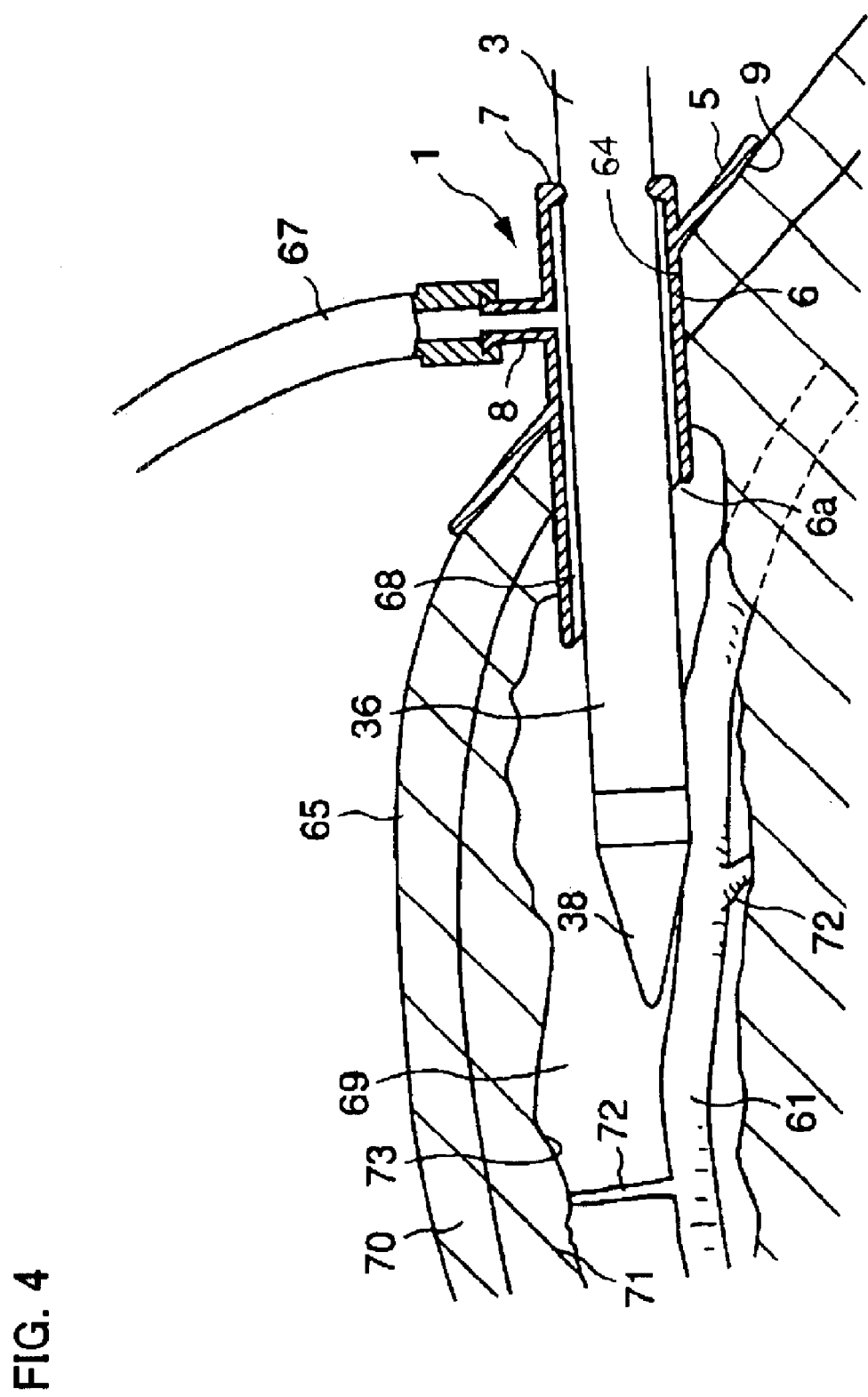
FIG. 4 is a cross-sectional view showing the state in which the trocar according to the first embodiment is fitted into the dissection portion of skin of the lower limb and a dissector is inserted into a cavity by using the trocar as a guide.

Then, as shown in FIG. 4, the operator inserts the dissecting portion 38 along the blood vessel 61, and when the dissecting portion 38 is inserted to a small extent, the operator inserts the guide tube 6 of the trocar 1 toward the inguinal region 63 obliquely (approximately in parallel with the blood vessel 61). When the tip 6a of the trocar 1 is turned downward, the adhesive layer 9 on the bottom surface 5a of the flange 5 is adhesively fixed to skin 65. In this state, the operator connects a gas feed tube 67 connected to a gas feed pump 66 to the gas feed connecting portion 8.

In this case, since the outer circumferential surface of the inserting tube 36 of the dissector 3 adheres closely to the gastight ring portion 7, the interior of the guide tube 6 and the interior of a cavity 69 is placed in a gastight state, and a gas feed passage 68 is established in an annular space between an inner surface of the guide tube 6 and the outer circumferential surface of the inserting tube 36.

The light guide connecting portion 33 of the rigid scope 4 is connected to a light source device 78 via a light guide cable 57. Accordingly, illuminating light can be projected from a tip portion of the rigid scope 4 to illuminate the interior of the cavity 69. When the gas feed pump 66 is driven, a gas is fed into the cavity 69 via the gas feed tube 67, the gas feed connecting portion 8 and the gas feed passage 68, whereby the cavity 69 is expanded.

At this time, in the cavity 69, a subcutaneous tissue 70 and a connective tissue of blood vessel 71 lie under the skin 65, and a blood vessel 61 exists under the connective tissue of blood vessel 71. The blood vessel 61 has a plurality of side branches 72, and the branch ends of the respective side branches 72 are connected to the connective tissue of blood vessel 71. Subcutaneous fat 73 adheres to the connective tissue of blood vessel 71.

Subsequently, the operator inserts the dissect or 3 more deeply in the expanded cavity 69 while guiding the dissector 3 by means of the guide tube 6. At this time, since the guide tube 6 is formed to extend obliquely with respect to the flange 5, the guide tube 6 can guide the dissector 3 obliquely with respect to the body surface, thereby successfully introducing the dissector 3 along the running direction of the blood vessel 61.

During the insertion of the dissector 3, while the operator is observing the cavity 69 on the monitor 76 to take care not to injure the blood vessel 61 nor the side branches 72, the operator gradually advances the dissector 3 by repeating the manipulation of pushing the dissector 3 to a small extent to dissect the connective tissue of blood vessel 71 from the blood vessel 61 and the side branches 72 by means of the dissecting portion 38 and then pulling the dissector 3 to a small extent. During this time, even if the dissector 3 is oscillated vertically and horizontally, the trocar 1 does not at all come off the skin 65, because the trocar 1 is fixed to the skin 65 by the adhesive layer 9. In addition, since the trocar 1 (the guide tube 6 and the flange 5) is formed of an elastic material, the trocar 1 can smoothly follow the movement of the dissector 3 owing to its elastic deformation (the trocar 1 can absorb the deformation of the body surface due to the movement of the dissector 3).

After the operator has inserted the dissector 3 along the blood vessel 61 from the knee 62 toward the inguinal region 63 and completed a dissecting operation with the dissector 3 in the above-described manner, the operator extracts the dissector 3 from the trocar 1. Then, as shown in FIG. 5, the operator inserts the therapeutic sheath 2 in which the rigid scope 4 is inserted, into the guide tube 6 of the trocar 1. At this time as well, the guide tube 6 which is formed to extend obliquely with respect to the flange 5 can guide the therapeutic sheath 2 obliquely with respect to the body surface, thereby successfully introducing the therapeutic sheath 2 along the running direction of the blood vessel 61.

When the operator grips the therapeutic sheath 2 in one hand and advances the holder manipulating portion 22 by using, for example, the thumb of the one hand, the blood vessel holder. 21 projects from the tip of the sheath body 10. In addition, when the operator advances the therapeutic instrument manipulating portion 19 by using the index finger of the one hand in which the therapeutic sheath 2 is gripped, the bipolar cutter 18 projects from the tip of the sheath body 10. Namely, the operator can move the blood vessel holder 21 and the bipolar cutter 18 back and forth while gripping the sheath body 10 in only one hand. Accordingly, the operator can easily sever the side branches 72 by means of the bipolar cutter 18 while holding the blood vessel 61 to be extracted, by means of the blood vessel holder 21. At this time as well, the trocar 1 (the guide tube 6 and the flange 5) which is formed of an elastic material can smoothly follow the movement of the therapeutic sheath 2 owing to its elastic deformation.

The operator repeats the operation of severing each of the side branches 72 to dissect the blood vessel 61 from the connective tissue of blood vessel 71, and when the operation advances up to the inguinal region 63, the operator completes severing the side branches 72. Then, the operator forms a small dissected portion of skin in the inguinal region 63 immediately above the blood vessel 61 by means of a scalpel or the like, and draws out the blood vessel 61 through this dissected portion of skin 64. The operator can sever the drawn portion of the blood vessel 61, and ligates both severed ends of the blood vessel 61 with a suture. Then, the operator performs the operation of extracting the portion of the blood vessel 61 that extends from the dissected portions of skin 64 of the knee 62 toward the ankle of the lower limb 60, thereby finally extracting a single blood vessel (about 60 cm long). The method of manipulation is basically the same as the above-described method of harvesting the portion of the blood vessel 61 that extends from the knee 62 to the inguinal region 63, and detailed explanation is omitted. The vessel which is cut its both sides is removed from the dissected portion of skin 64.

As described above, the trocar 1 according to the first embodiment is provided with the flange 5 which is to be adhesively fixed to the body surface. Accordingly, the trocar 1 does not need to have a complicated stopper structure such as a balloon or an expanding portion, and makes it possible to prevent the guide tube 6 from coming off, merely by adhesively fixing the flange 5 to the body surface. Namely, the trocar 1 according to the first embodiment is inexpensive in that the guide tube 6 can be effectively prevented from coming off, by means of a simple construction.

In addition, in the trocar 1 according to the first embodiment, the flange 5 is provided on the guide tube 6 so as to make a predetermined angle (except zero degrees) with a plane approximately perpendicular to the axial direction of the guide tube 6. In other words, the guide tube 6 extends through the flange 5 obliquely with respect to the extending direction of the flange 5. Accordingly, the guide tube 6 can guide an endoscope, a therapeutic instrument and the like obliquely with respect to the body surface. Therefore, the operator can make observations in various directions through an endoscope inserted through the guide tube 6, and can also guide an endoscope and a therapeutic instrument in various directions as occasion demands. Particularly in the case of the first embodiment used for the extraction of a blood vessel, the dissector 3 can be guided obliquely with respect to the body surface, thereby successfully introducing the dissector 3 along the running direction of the blood vessel 61.

In addition, since the flange 5 is provided on the outer circumference of the guide tube 6 at a location other than the opposite ends thereof, a part of the guide tube 6 is exposed outside the body of the patient when the trocar 1 is inserted in the patient. Accordingly, the operator can easily grip the trocar 1 with good operability.

The trocar 1 according to the first embodiment is provided with, in addition to the stopper structure (the flange 5), the gastightness retaining member (sealing member) 7 which retains the gastightness of the gap between the circumferential surface of the internal hole of the guide tube 6 and an outer surface of an endoscope or a therapeutic instrument inserted in the internal hole (or conduit) of the guide tube 6. Accordingly, the trocar 1 can reliably retain the gastightness of a body cavity, this feature is particularly important for endoscopic surgical operation.

In addition, since the trocar 1 according to the first embodiment is formed of an elastic material, the whole of the trocar 1 can smoothly follow the movement of the dissector 3 owing to its elastic deformation (the trocar 1 can absorb the deformation of the body surface due to the movement of the dissector 3).

Furthermore, since the trocar 1 is formed of an elastic material, the angle made by the flange 5 with the axis of the guide tube 6 is variable within an elastically allowable range. Accordingly, when the trocar 1 is inserted in the patient, the flange 5 can easily adhere to the body surface of the patient. As a matter of course, the angle made by the flange 5 with the axis of the guide tube 6 can also be made variable by using a mechanical joint (for example, the guide tube 6 is inserted through a spherical member and a flange having a center opening which diameter is smaller than the diameter of the spherical member and larger than the diameter of the guide tube 6 is fitted onto the guide tube 6 as the flange 5).

Incidentally, in the first embodiment, the whole of the trocar 1 is formed of an elastic material, but at least one of the flange 5 and the guide tube 6 or at least a part of the flange 5 or at least a part of the guide tube 6 may be formed of an elastic material. Means for fixing the flange 5 to the body surface is not limited to adhesion, and any fixing means that can easily fix the flange 5 to the body surface may be used. In addition, the gastightness retaining member (sealing member) 7 need not be an O-ring such as that used in the first embodiment, and may have any construction that can retain the gastightness of the body cavity.

FIGS. 6 to 18 show other embodiments of the invention (a second embodiment to a seventh embodiment). In these embodiments, constituent portions common to the first embodiment are denoted by the same reference numerals as those used in the first embodiment, and the description of the same constituent portions is omitted.

Figure 6:
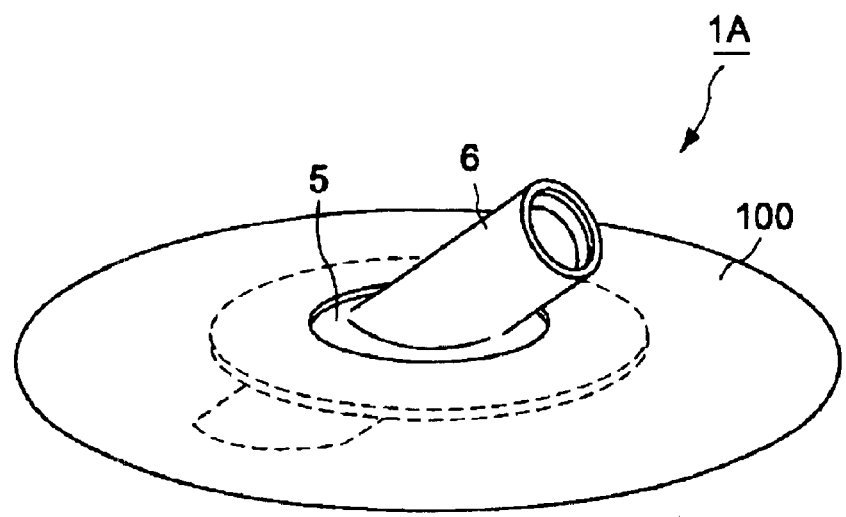
FIG. 6 is a perspective view of a trocar according to a second embodiment of the invention.
Figure 7:
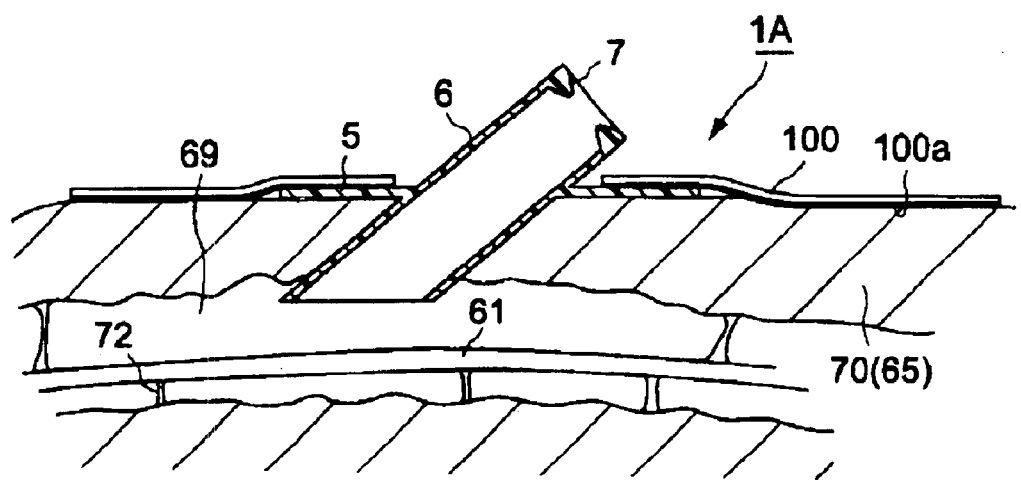
FIG. 7 is a cross-sectional view showing the manner in which the trocar shown in FIG. 6 is used.

FIGS. 6 and 7 show a trocar 1A according to the second embodiment of the invention. The trocar 1A according to the second embodiment does not have the adhesive layer 9 provided on the bottom surface 5a of the flange 5. Instead, an adhesive seal 100 having an adhesive layer 100a is stuck to the flange 5, and as shown in FIG. 7, the flange 5 is fixed to the body surfaces 65 and 70 by using the, adhesive seal 100. Incidentally, the constructions of the other portions are the same as those in the first embodiment.

According to the construction of the second embodiment, since the adhesive layer 9 is not provided, it is possible to produce the trocar 1A itself more easily, and as long as the adhesive seal 100 has elasticity, the trocar 1A can follow the movement of an endoscope and a therapeutic instrument to some extent even if neither the flange 5 nor the guide tube 6 has elasticity. For example, the seal 100 is a polyurethane film on one side of which hypoallergenic acrylic adhesive is applied. In this case, the seal 100 has elasticity since polyurethane is used as a base material.

Figure 8:
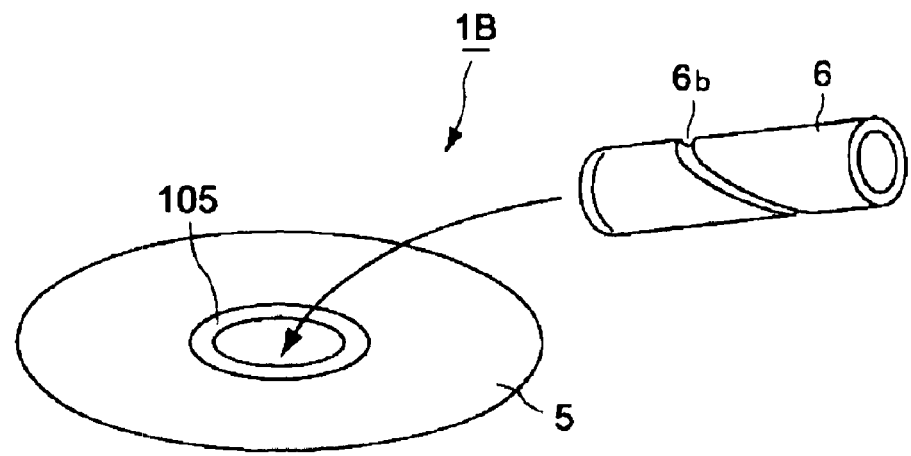
FIG. 8 is a perspective view of a trocar according to a third embodiment of the invention.
Figure 9:
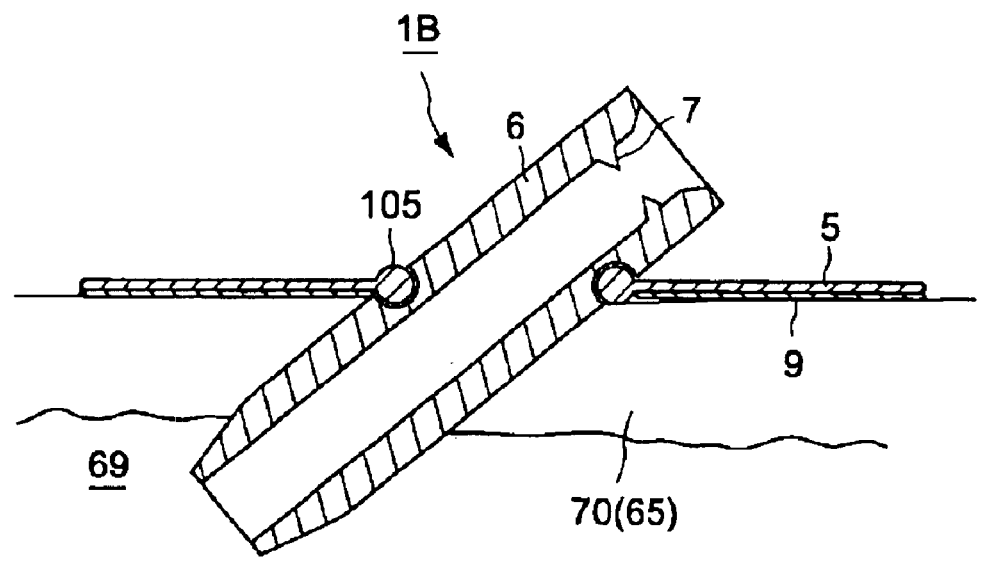
FIG. 9 is a cross-sectional view showing the manner in which the trocar shown in FIG. 8 is used.

FIGS. 8 and 9 show a trocar 1B according to the third embodiment of the invention. As shown in FIG. 8, the trocar 1B according to the third embodiment is constructed so that the flange 5 and the guide tube 6 can be separated from each other. Specifically, a fixed ring 105 is provided on the inner circumference of the ring-shaped flange 5, and an engaging groove 6b which engages with the fixed ring 105 is formed on the outer circumferential surface of the guide tube 6. The engaging groove 6b obliquely extends to make a predetermined angle with a plane perpendicular to the direction of the longitudinal axis of the guide tube 6, and the engaging groove 6b is arranged to direct the guide tube 6 obliquely with respect to the extending direction of the flange 5 when the engaging groove 6b engages with the fixed ring 105 (the flange 5 is arranged to be directed by the engaging groove 6b so that the flange 5 makes a predetermined angle with a plane approximately perpendicular to the axial direction of the guide tube 6). In addition, since the engagement is so tight, a seal capable of fully retaining the gastightness of a body cavity is formed when the engaging groove 6b and the fixed ring 105 are engaged with each other. Incidentally, the constructions of the other portions are the same as those in the first embodiment. The flange 5 and fixed ring 105 are elastomers or a soft thermoplastic which can be plastically deformed to stretch over the guide tube. When the flange 5 is fixed to the guide tube 6, the flange 5 and fixed ring 105 are extended until the fixed ring 105 corresponds with the groove 6b, at which point, the flange is relaxed and the fixed ring 105 engages with the groove 6b.

FIG. 9 shows the state in which the guide tube 6 which is fitted in the flange 5 is fixed to the body surfaces 65 and 70. As shown, the guide tube 6 extends obliquely with respect to the body surfaces 65 and 70, whereby the third embodiment can serve effects and advantages similar to those of the first embodiment.

According to the third embodiment, since the guide tube 6 and the flange 5 can be separated in the above-described manner, the trocar 1B is superior in ease of cleaning and ease of storage, and is also easy to manufacture. In addition, the trocar 1B is useful in that the flange 5 and the guide tube 6 can be formed of different materials. In addition, the engaging portion of the guide tube 6 may use spaced projections (not shown) instead of the engaging groove 6b where the fixed ring 105 is captured between the spaced projections.

Figure 10:
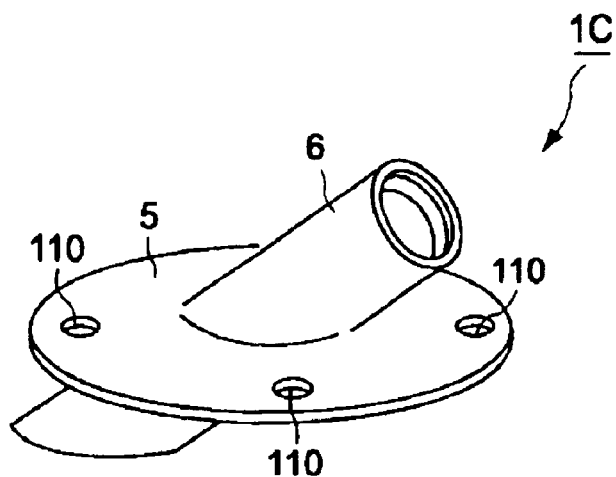
FIG. 10 is a perspective view of a trocar according to a fourth embodiment of the invention.
Figure 11:
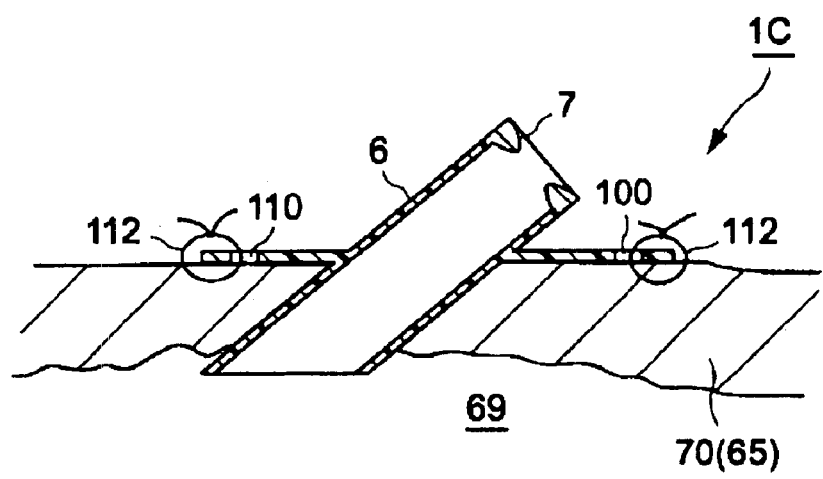
FIG. 11 is a cross-sectional view showing the manner in which the trocar shown in FIG. 10 is used.

FIGS. 10 and 11 show a trocar 1C according to the fourth embodiment of the invention. As shown in FIG. 10, the trocar 1C according to the fourth embodiment does not have the adhesive layer 9 provided on the bottom surface of the flange 5. Instead, a plurality of holes 110 for tying sutures are formed in the flange 5. Incidentally, the constructions of the other portions are the same as those in the first embodiment.

According to the construction of the fourth embodiment, as shown in FIG. 11 by way of example, after a needle (not shown) with a suture 112 has been stuck into the body surfaces 65 and 70, the needle is passed through one of the holes 110 of the flange 5 and both ends of the suture 112 are tied together, whereby the flange 5 can be fixed to the body surfaces 65 and 70 by the sutures 112.

Figure 12:
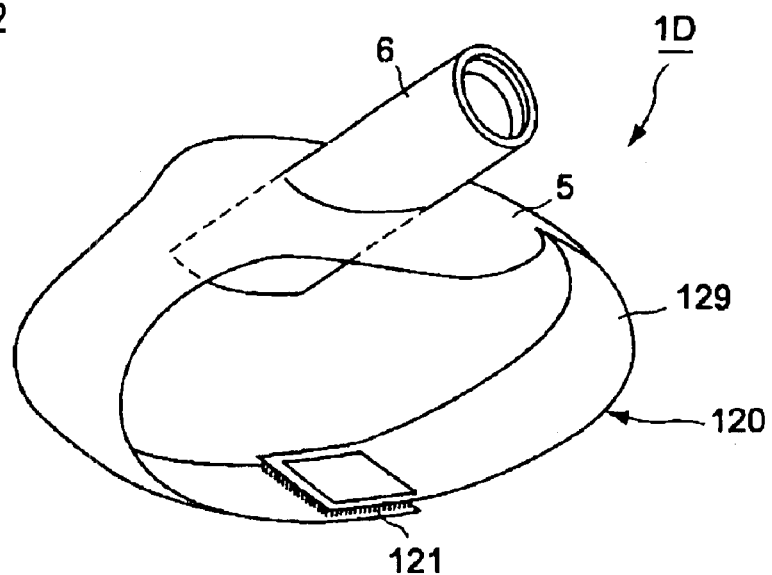
FIG. 12 is a perspective view of a trocar according to a fifth embodiment of the invention.
Figure 13:
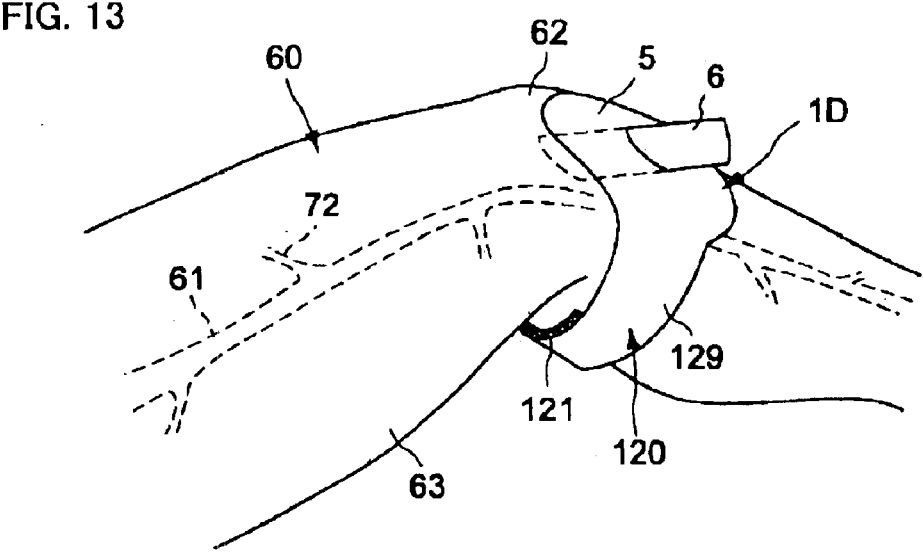
FIG. 13 is a cross-sectional view showing the manner in which the trocar shown in FIG. 12 is used.

FIGS. 12 and 13 show a trocar 1D according to the fifth embodiment of the invention. As shown in FIG. 12, the trocar 1D according to the fifth embodiment has a construction in which a band 129 extending from the flange 5 has a Hook-and-Loop fastener (for example, Velcro fastener) 121 whose fastening halves are respectively provided at the opposite ends of the band 129. Namely, the flange 5 and the band 129 form a fixing belt 120 for fixing the guide tube 6 to a living body. Incidentally, the constructions of the other portions are the same as those in the first embodiment. The band 129 is made of elastomer or soft thermoplastic, and is attached to the guide tube 6 like flange 5 in the third embodiment.

According to the construction of the fifth embodiment, as shown in FIG. 13, it is possible to prevent the guide tube from coming off, by winding the fixing belt 120 around, for example, the knee 62 of the lower limb 60.

Accordingly, since the trocar 1D according to the fifth embodiment has belt-like stopper means, the trocar 1D can be reliably fixed, and is particularly suited to an arm, a leg and the like.

Figure 14:
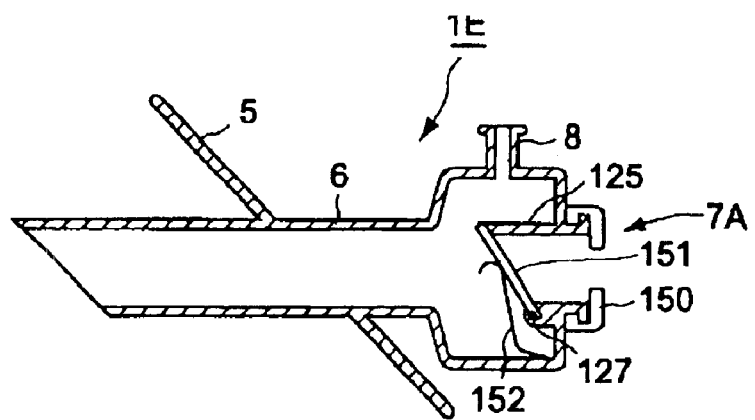
FIG. 14 is a perspective view of a trocar according to a sixth embodiment of the invention.

FIG. 14 shows a trocar 1E according to the sixth embodiment. In the trocar 1E according to the sixth embodiment, the gastightness retaining member (sealing member) provided in the guide tube 6 is formed as a valve 7A. Specifically, a tubular support portion 125 which supports a valve flap 151 in a turnable manner extends to project into the guide tube 6 from the operator side of the guide tube 6, and a member (for example an elastic body) 150 which comes into pressure contact with the outer circumferential surface of an endoscope or a therapeutic instrument to be inserted into the guide tube 6 is fitted to the external end of the support portion 125. Incidentally, the valve flap 151 can open and close the passage of the guide tube 6 by turning about a pivot 127 provided in the support portion 125. In addition, the valve flap 151 is biased in the closing direction by a spring 152. The constructions of the other portions are the same as those in the first embodiment.

According to the construction of the sixth embodiment, when an endoscope or a therapeutic instrument is inserted into the support portion 125 to press the valve flap 151, the valve flap 151 is turned and opened against the urging force of the spring 152, whereby the endoscope or the therapeutic instrument can be inserted through the guide tube 6. In this case, since the elastic body 150 comes into pressure contact with the outer circumferential surface of the endoscope or the therapeutic instrument, the gastightness of the body cavity can be retained. In addition, even after the endoscope or the therapeutic instrument has been removed from the guide tube 6, the gastightness of the body cavity can still be retained, because the valve flap 151 is closed by the biasing force of the spring 152.

Figure 17:
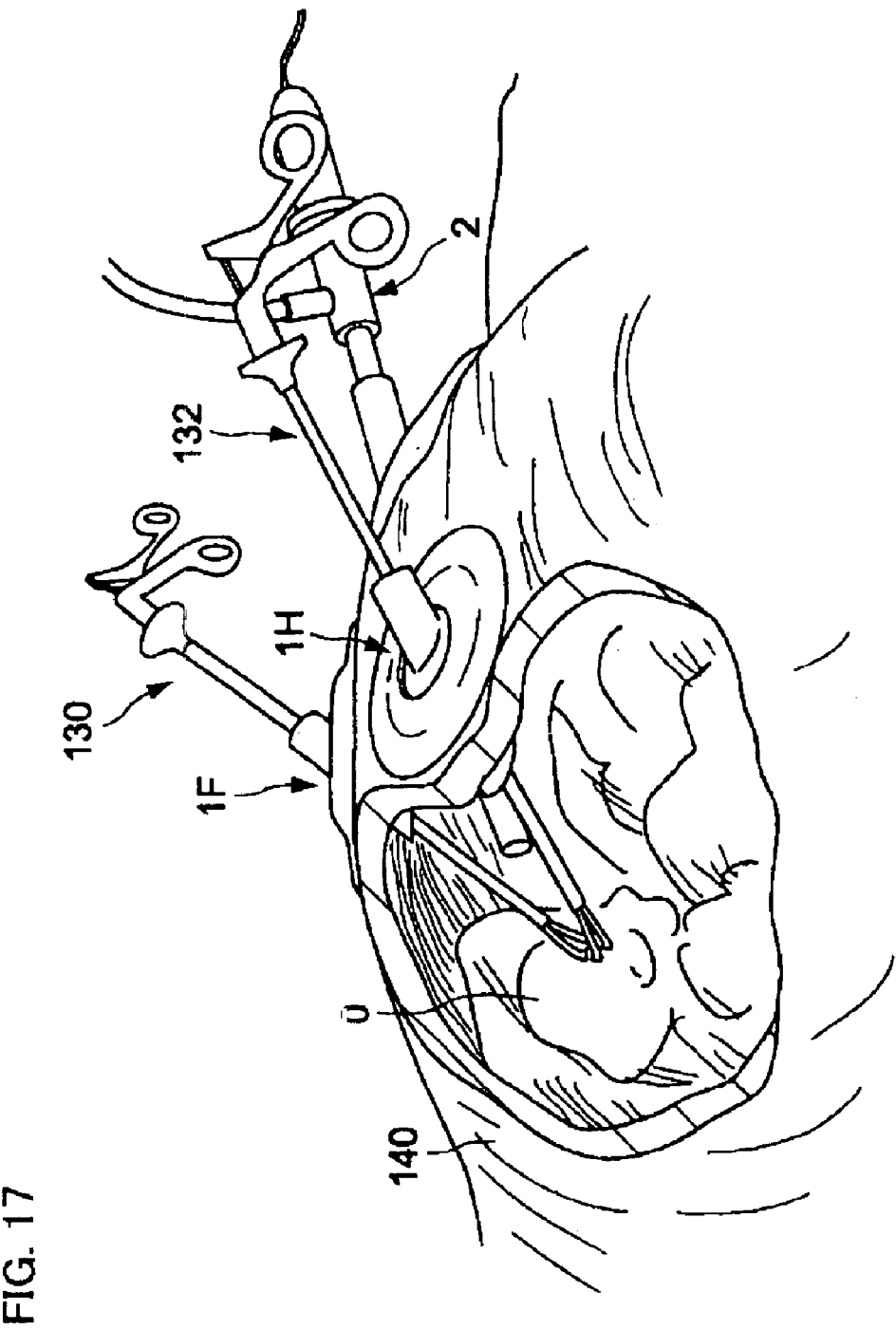
FIG. 17 is a perspective view showing the manner in which the trocars shown in FIGS. 15A to 15C are used.

FIGS. 15A to 15C respectively show a plurality of trocars 1F, 1G and 1H which differ in the inclination angle of the guide tube 6 to the flange 5. These trocars 1F, 1G and 1H are used for introducing a plurality of operating instruments 130, 2, and 132, respectively, into the body of a patient, and the operating instruments 130, 2, and 132 differ in access direction relative to a therapeutic target part (affected part) O (hence, in inclination angle relative to the body surface) as shown in FIG. 16. The therapeutic target part O to be accessed may be an organ inside an abdominal wall 140 as shown in FIG. 17, or may also be the blood vessel 61 inside the lower limb 60 as described previously. Accordingly, the kind of area to which the trocar according to the invention can be applied is not at all be limited.

Figure 18A:
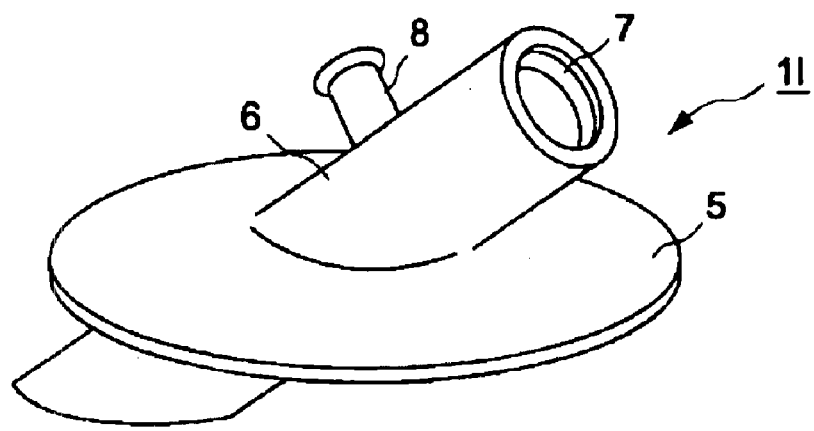
FIG. 18A is a perspective view of a trocar according to a seventh embodiment of the invention.
Figure 18B:
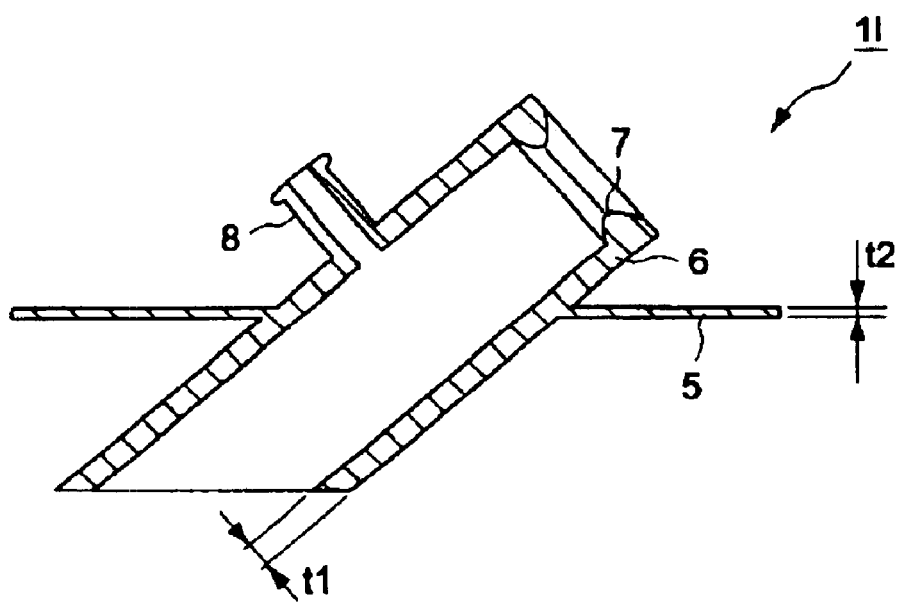
FIG. 18B is a cross-sectional view of the trocar shown in FIG. 18A.

FIGS. 18A and 18B show a trocar 1I according to the seventh embodiment of the invention. As clearly shown in FIG. 18A, in the trocar 1I according to the seventh embodiment, a wall thickness t2 of the flange 5 is set to be thinner than a wall thickness t1 of the guide tube 6. Incidentally, the constructions of the other portions are the same as those in the first embodiment.

Incidentally, in the case where the wall thickness of the flange 5 is not constant or the wall thickness of the guide tube 6 is not constant, the wall thickness of the guide tube 6 may be determined from the average wall thickness of the portion of the guide tube 6 that is to be inserted into a living body, while the wall thickness of the flange 5 may be determined from the average wall thickness of the portion of the flange 5 that is to come into contact with a living body.

According to the construction of the seventh embodiment, the guide tube 6 can be easily inserted into a dissected portion of skin, and the flange 5 can be easily made to adhere to the skin.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A trocar for endoscopic operation, comprising:

a guide tube for introducing a medical instrument into a living body, the guide tube having a straight shape relative to a longitudinal axis; and a flange provided on an outer circumference of the guide tube, the flange having a contact surface which comes into contact with an outer surface of a living body, the flange being oblique with respect to the longitudinal axis of the guide tube and positioned at a location other than at a proximal and distal end of the guide tube such that a portion of the guide tube is exposed outside the outer surface of the living body when the trocar is inserted therein.

2. A trocar according to claim 1, wherein the guide tube and the flange are integrally formed.

3. A trocar according to claim 1, wherein at least a portion of the trocar is formed of an elastic material.

4. A trocar according to claim 1, further comprising a fixing portion for fixing the trocar to the living body.

5. A trocar according to claim 4, wherein the fixing portion is an adhesive layer provided on the contact surface of the flange.

6. A trocar according to claim 4, wherein the fixing portion is an adhesive sheet having at least a portion wider in area than the flange and adhered to a surface of the flange opposite to the contact surface.

7. A trocar according to claim 4, wherein the fixing portion is a band extending from the flange.

8. A trocar according to claim 1, wherein the flange has at least one hole through which to pass a suture.

9. A trocar according to claim 1, wherein the flange is removably secured to the guide tube.

10. A trocar according to claim 1, wherein a gastightness retaining member is provided in an interior of the guide tube.

11. A trocar according to claim 1, wherein the wall thickness of the flange differs from that of the guide tube.

* * * * *